(12) United States Patent
Sulsky et al.

(10) Patent No.: US 6,670,380 B2
(45) Date of Patent: Dec. 30, 2003

(54) PYRIDONE INHIBITORS OF FATTY ACID BINDING PROTEIN AND METHOD

(75) Inventors: Richard Sulsky, West Trenton, NJ (US); Jeffrey A. Robl, Newtown, PA (US)

(73) Assignee: Bristol-Myers Squibb Co., Princeton, NJ (US)

( * ) Notice: Subject to any disclaimer, the term of this patent is extended or adjusted under 35 U.S.C. 154(b) by 0 days.

(21) Appl. No.: 09/989,212

(22) Filed: Nov. 20, 2001

(65) Prior Publication Data

US 2002/0077340 A1 Jun. 20, 2002

Related U.S. Application Data

(60) Provisional application No. 60/252,014, filed on Nov. 20, 2000.

(51) Int. Cl.[7] ............... A61K 31/4412; A61K 31/4427; C07D 213/64; C07D 213/80; A61P 3/10
(52) U.S. Cl. ............... 514/345; 514/350; 514/340; 514/336; 514/335; 514/334; 514/333; 514/332; 546/298; 546/296; 546/290; 546/268.4; 546/268.1; 546/261; 546/256; 546/302; 546/303
(58) Field of Search ............... 546/298, 303, 546/256, 261, 268.4, 296, 302; 514/350, 340, 336, 335, 334, 333, 332, 345

(56) References Cited

U.S. PATENT DOCUMENTS

| | | |
|---|---|---|
| 4,275,069 A | 6/1981 | Youngdale |
| 5,627,210 A | 5/1997 | Valerio et al. |

FOREIGN PATENT DOCUMENTS

| | | |
|---|---|---|
| DE | 3627246 | 2/1988 |
| WO | WO 96/38421 | 12/1996 |
| WO | WO 99/32448 | 7/1999 |
| WO | WO 00/15229 | 3/2000 |
| WO | WO 00/15230 | 3/2000 |
| WO | WO 00/59506 | 10/2000 |
| WO | WO 01/54694 | 8/2001 |

OTHER PUBLICATIONS

Reese–Wogoner A et al. Biochim Biophys Acta (1999) 1441(2–3):106–16.*
Ghosez L et al. Tetrahedron (1999) 55:3387–3400.*
Angelino SAGF et al. Bio–Organic Heterocycles. (1984) 18:281–284.*
CAPLUS 105: 93875/DN.
Shibata, K., Agric. Biol. Chem. vol. 53, No. 12, pp. 3355–3356 (1989).
CAPLUS 136:53682/DN.
Gotthardt, H. et al., Chem. Ber. vol. 119, pp. 1315–1330 (1986).

* cited by examiner

*Primary Examiner*—Evelyn Mei Huang
(74) *Attorney, Agent, or Firm*—Laurelee A. Duncan

(57) ABSTRACT

Compounds are provided having the formula:

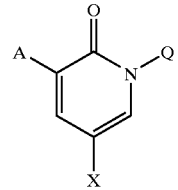

wherein A, Q, and X are as described herein.

A method is also provided for treating diabetes and related diseases, especially Type II diabetes, employing such compounds alone or in combination with other antidiabetic agents such as metformin, glyburide, troglitazone and/or insulin.

14 Claims, No Drawings

PYRIDONE INHIBITORS OF FATTY ACID BINDING PROTEIN AND METHOD

This application claims priority to U.S. Provisional Application Serial No. 60/252,014 filed on Nov. 20, 2000, the entirety of which is incorporated herein by reference.

FIELD OF THE INVENTION

The present invention relates to pyridones which are inhibitors of fatty acid binding protein (especially aP2) and to a method for treating diabetes, especially Type II diabetes, as well as hyperglycemia, hyperinsulinemia, obesity, Syndrome X, diabetic complications, atherosclerosis and related diseases, and other chronic inflammatory and autoimmune/inflammatory diseases, employing such pyridones alone or in combination with one or more types of therapuetic agents. In addition, the compounds of the present invention act as inhibitors of aldose reductase and thus are useful in the treatment of diabetic complications such as diabetic retinopathy, diabetic neuropathy and diabetic nephropathy.

BACKGROUND OF THE INVENTION

Fatty acid binding proteins (FABPs) are small cytoplasmic proteins that bind to fatty acids such as oleic acids which are important metabolic fuels and cellular regulators. Dysregulation of fatty acid metabolism in adipose tissue is a prominent feature of insulin resistance and the transition from obesity to non-insulin dependent diabetes mellitus (NIDDM or Type II diabetes).

aP2 (adipocyte fatty binding protein), an abundant 14.6 KDa cytosolic protein in adipocytes, and one of a family of homologous intracellular fatty acid binding proteins (FABPs), is involved in the regulation of fatty acid trafficking in adipocytes and mediates fatty acid fluxes in adipose tissue. G. S. Hotamisligil et al, "Uncoupling of Obesity from Insulin Resistance Through a Targeted Mutation in aP2, the Adipocyte Fatty Acid Binding Protein", Science, Vol. 274, Nov. 22, 1996, pp. 1377–1379, report that aP2-deficient mice placed on a high fat diet for several weeks developed dietary obesity, but, unlike control-mice on a similar diet, did not develop insulin resistance or diabetes. Hotamisligil et al conclude "aP2 is central to the pathway that links obesity to insulin resistance" (Abstract, page 1377).

U.S. application Ser. No. 60/100,677, filed September 17, 1998, U.S. application Ser. No. 60/127,745 filed Apr. 5, 1999, and U.S. application Ser. No. 60/178,598 filed Jan. 28, 2000 disclose methods for treating diabetes employing an aP2 inhibitor.

DESCRIPTION OF THE INVENTION

In accordance with the present invention, pyridone compounds are provided which have the structure of formula I

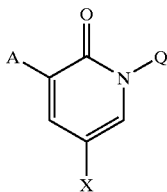

I including pharmaceutically acceptable salts thereof, prodrug esters thereof, and all stereoisomers thereof, wherein A is selected from
—$R^1$,
—$(CR^3R^4)_n$—$R^1$,
—$(CR^3R^4)_m R^5 (CR^6R^7)$—$R^1$, and
—$(CR^3R^4)_n (CR^6R^7)_p$—$R^1$;

Q is selected from
—$R^2$,
—$(CR^3R^4)_n R^2$,
—$R^5(CR^3R^4)_p$—$R^2$,
—$(CR^{11}R^{12})_m R^5 (CR^6R^7)_p$—$R^2$,
—$(CR^{11}R^{12})_n (CR^6R^7)_p$—$R^2$,
—$S(O)R^2$ where $R^2$ is other than hydrogen, and
—$S(O_2)R^2$ where $R^2$ is other than hydrogen;

$R^1$ and $R^2$ are the same or different and are independently selected from hydrogen, alkyl, substituted alkyl, cycloalkyl, substituted cycloalkyl, alkenyl, substituted alkenyl, cycloalkenyl, substituted cycloalkenyl, aryl, substituted aryl, heteroaryl, substituted heteroaryl, aralkyl, substituted aralkyl, heteroaralkyl, substituted heteroaralkyl, cycloheteroalkyl and substituted cycloheteroalkyl;

$R^3$ and $R^4$ are the same or different and are independently selected from H, alkyl, cycloalkyl, alkenyl, cycloalkenyl, alkynyl, alkoxycarbonyl, alkylcarbonyl, aminocarbonyl, alkylaminocarbonyl, arylaminocarbonyl, arylcarbonyl, aryl and heteroaryl, halo, hydroxy, alkoxy and aryloxy;

or $R^3$ and $R^4$ together with the atom to which they are bonded may form a 3 to 9-membered saturated or unsaturated ring;

$R^5$ is a bond, O, $NR^8$, S, SO, $SO_2$, CO or CONH;

$R^6$ and $R^7$ are the same or different and are independently selected from H, alkyl, cycloalkyl, aryl, hydroxy, amino, halo, alkoxy, aryloxy, alkylthio, arylthio, alkylamino, dialkylamino, arylamino, diarylamino, alkoxycarbonyl, alkylaminocarbonyl or alkylcarbonylamino;

$R^8$ is H, aryl, arylcarbonyl, alkylaminocarbonyl, arylaminocarbonyl, alkoxycarbonyl, aryloxycarbonyl, alkyl or alkylcarbonyl;

$R^9$ is H, alkyl, cycloalkyl, aryl, aralkyl, heteroaryl or a prodrug ester thereof;

$R^{10}$ is H, alkyl, cycloalkyl, aryl, aralkyl, heteroaryl or a prodrug ester thereof;

$R^{11}$ and $R^{12}$ are independently selected from hydrogen, alkyl, substituted alkyl, cycloalkyl, substituted cycloalkyl, alkenyl, substituted alkenyl, cycloalkenyl, substituted cycloalkenyl, aryl, substituted aryl, heteroaryl, substituted heteroaryl, aralkyl, substituted aralkyl, heteroaralkyl, substituted heteroaralkyl, cycloheteroalkyl and substituted cycloheteroalkyl;

X is selected from -Z, —$(CR^3R^4)_n$-Z, —CH=CHZ, and -(cycloalkyl)-Z;

Z is —$CO_2R^9$, —CONHOH, —$CONR^9R^{10}$, —$(CR^3R^4)_m$OH, tetrazole of the formula

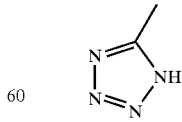

or its tautomer; and when X is other than Z, Z is additionally selected from —$SO_3H$, and —$PO_3R^9R^{10}$, n is an integer selected from 0 to 5;
m is an integer selected from 1 to 5; and
p is an integer selected from 0 to 4.

In addition, the present invention provides for novel intermediates useful in the synthesis of compounds of formula I. Such intermediates have the structure of formula II $$II$$

where A and Q are as defined above,
X* is -W, —$(CR^3R^4)_n$-W, —CH=CHW, or -(cycloalkyl)-W; and
W is cyano, —C(O)Cl, or —C(O)H, and when W is other than X*, W is additionally selected from halogen, hydroxy, or alkenyl.

In addition, in accordance with the present invention, a method is provided for treating diabetes, especially Type II diabetes, and related diseases such as insulin resistance, hyperglycemia, hyperinsulinemia, elevated blood levels of fatty acids or glycerol, obesity, hypertriglyceridemia, atherosclerosis, inflammation, diabetic retinopathy, diabetic neuropathy and diabetic nephropathy wherein a therapeutically effective amount of a compound of structure I is administered to a human patient in need of treatment.

In addition, in accordance with the present invention, a method is provided for treating diabetes and related diseases as defined above and hereinafter, wherein a therapeutically effective amount of a combination of a compound of structure I and another type antidiabetic agent is administered to a human patient in need of treatment.

In the above method of the invention, the compound of structure I will be employed in a weight ratio to another antidiabetic agent (depending upon its mode of operation) within the range from about 0.01:1 to about 100:1, preferably from about 0.1:1 to about 10:1.

Examples of X moieties include (but are not limited to)

Preferred compounds of formula I include compounds where
A is $R^1$ or $(CR^3R^4)_n$—$R^1$ where n is 1 and $R^3$ and $R^4$ are the same or different and are selected from hydrogen, alkyl and substituted alkyl;
$R^1$ is aryl, substituted aryl, heteroaryl, substituted heteroaryl, alkyl or cycloalkyl;
Q is $R^2$ or $(CR^3R^4)_n$—$R^2$ where n is 1 and $R^3$ and $R^4$ are the same or different and are selected from hydrogen, alkyl and substituted alkyl;
$R^2$ is aryl, substituted aryl, cycloalkylalkyl, heteroaryl or substituted heteroaryl;

X is $(CR^3R^4)_n$-Z where n is 0 or 1 and $R^3$ and $R^4$ are the same or different and are selected from hydrogen, hydroxy, alkyl and substituted alkyl; and Z is $CO_2R^9$, $CONH_2$, $PO_3H_2$, $CONHOH$, or tetrazole.

More preferred compounds of formula I include compounds where

A is $R^1$;
$R^1$ is aryl (especially where aryl is phenyl), or substituted aryl (especially where substituted with one or more halogen, alkoxy or aryloxy);
Q is $(CR^3R^4)_n$—$R^2$ where n is 1 and $R^3$ and $R^4$ are hydrogen
$R^2$ is aryl (especially where aryl is phenyl or napthyl), or substituted aryl (especially substituted with one or more halogen, alkyl, substituted alkyl alkoxy; arylalkoxy, or cyano);
X is —$(CR^3R^4)_n$-Z where n is 0 or 1 and $R^3$ and $R^4$ are hydrogen; and
Z is $CO_2H$, or tetrazole.

Most preferred compounds of formula I include compounds where

A is $R^1$;
$R^1$ is substituted aryl (especially where aryl is phenyl and the substituents are selected from halogens);
Q is $(CR^3R^4)_n$—$R^2$ where n is 1 and $R^3$ and $R^4$ are hydrogen
$R^2$ is aryl (especially where aryl is phenyl or napthyl), or substituted aryl (especially where the substituents are selected from halogen, and alkoxy);
X is —$(CR^3R^4)_n$-Z where n is 1 and $R^3$ and $R^4$ are hydrogen; and
Z is $CO_2H$.

DETAILED DESCRIPTION OF THE INVENTION

Compounds of the invention of general structure I may be synthesized as illustrated in the schemes set forth below.

Scheme 1

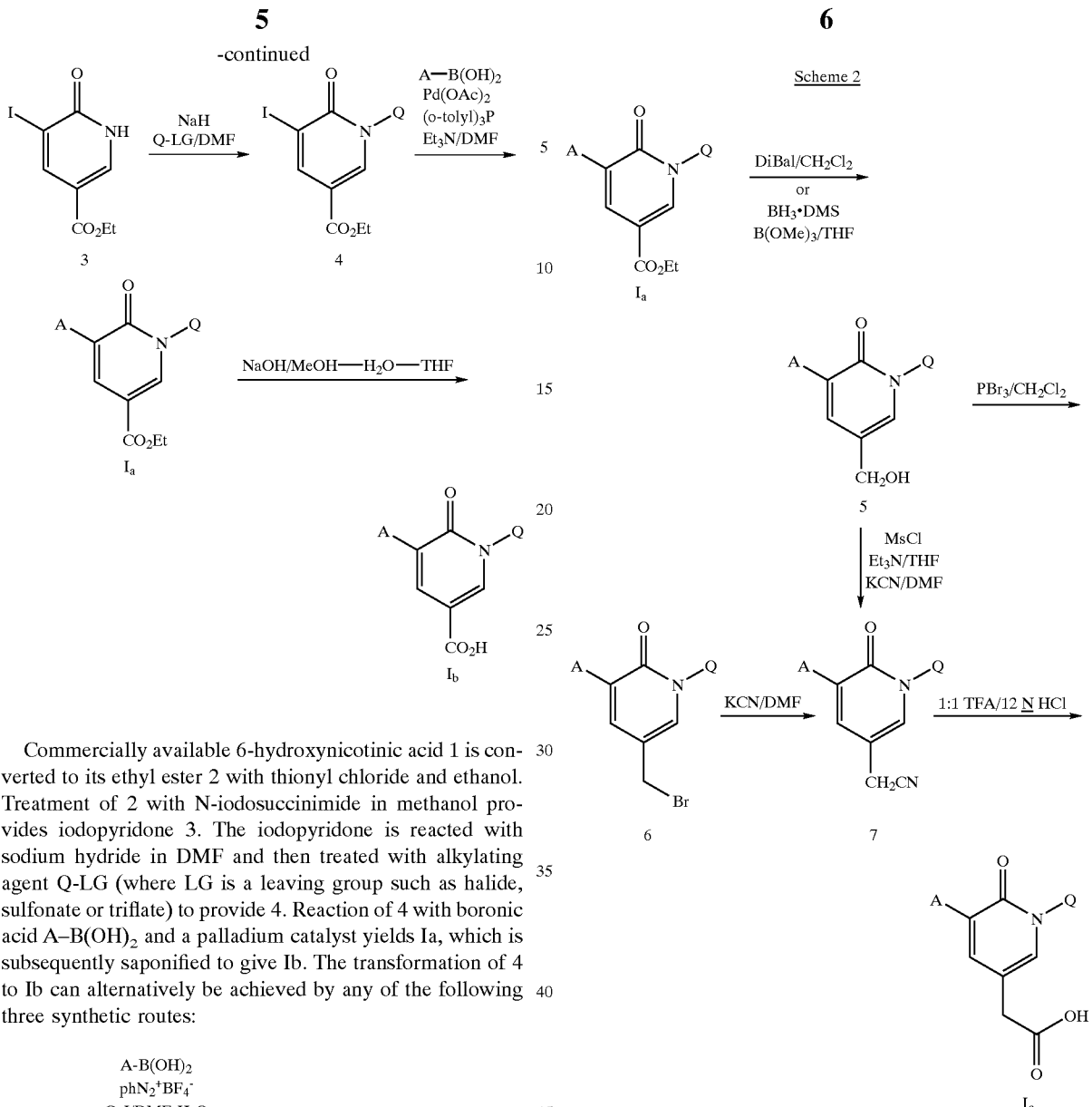

Commercially available 6-hydroxynicotinic acid 1 is converted to its ethyl ester 2 with thionyl chloride and ethanol. Treatment of 2 with N-iodosuccinimide in methanol provides iodopyridone 3. The iodopyridone is reacted with sodium hydride in DMF and then treated with alkylating agent Q-LG (where LG is a leaving group such as halide, sulfonate or triflate) to provide 4. Reaction of 4 with boronic acid A–B(OH)$_2$ and a palladium catalyst yields Ia, which is subsequently saponified to give Ib. The transformation of 4 to Ib can alternatively be achieved by any of the following three synthetic routes:

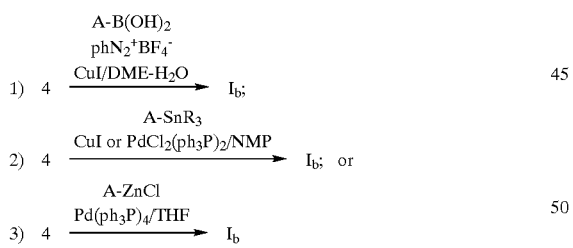

Additional compounds within formula I can be generated from compounds disclosed in scheme 1 through conversion of the substituent groups to other functionality by the usual methods of chemical synthesis, as illustrated in the following schemes 2 through 7, and the following examples. In generating such additional compounds one skilled in the art will recognize that it may be necessary to protect reactive functionality such as hydroxy, amino, thio or carboxy groups, where these are desired in the final product, to avoid their unwanted participation in reactions. The introduction and removal of protecting groups are well known to those skilled in the art (for example see Green, T. W., "Protective Groups in Organic Synthesis", John Wiley and Sons 1991).

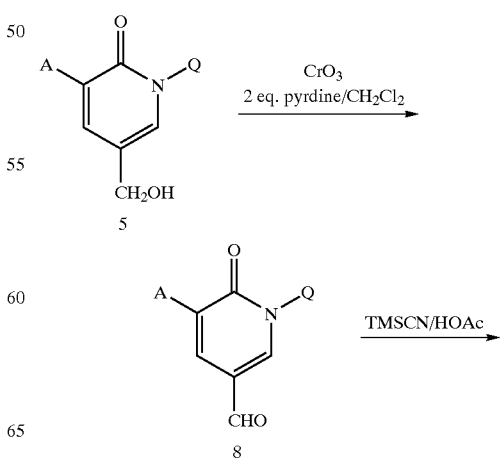

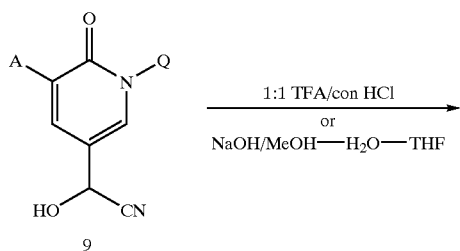

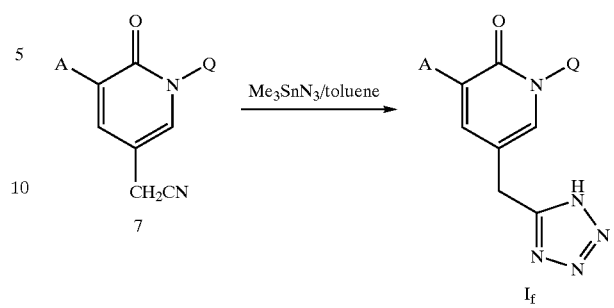

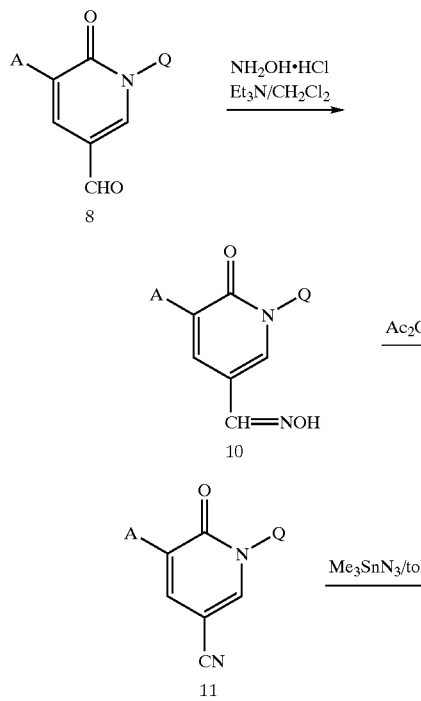

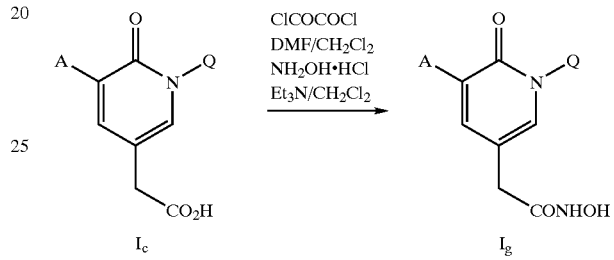

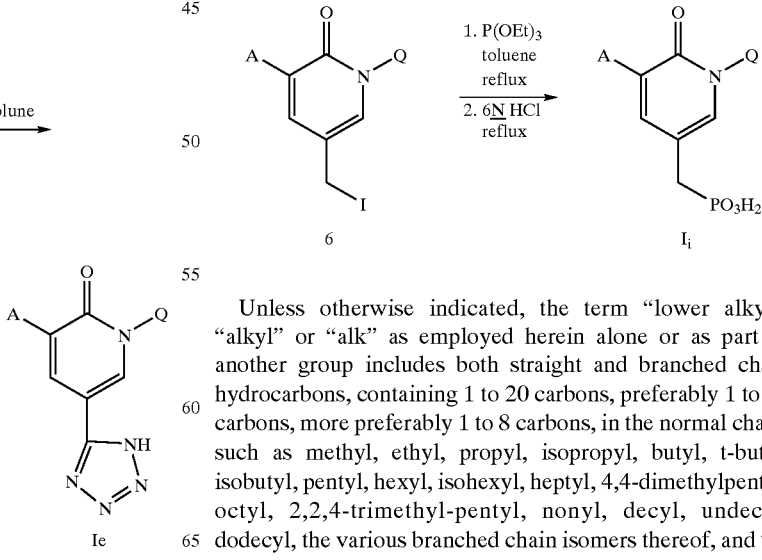

Unless otherwise indicated, the term "lower alkyl", "alkyl" or "alk" as employed herein alone or as part of another group includes both straight and branched chain hydrocarbons, containing 1 to 20 carbons, preferably 1 to 10 carbons, more preferably 1 to 8 carbons, in the normal chain, such as methyl, ethyl, propyl, isopropyl, butyl, t-butyl, isobutyl, pentyl, hexyl, isohexyl, heptyl, 4,4-dimethylpentyl, octyl, 2,2,4-trimethyl-pentyl, nonyl, decyl, undecyl, dodecyl, the various branched chain isomers thereof, and the like as well as such groups including 1 to 4 substituents such as halo, for example F, Br, Cl or I or CF$_3$, alkoxy, aryl, aryloxy, aryl(aryl) or diaryl, arylalkyl, arylalkyloxy, alkenyl, cycloalkyl, cycloalkylalkyl, cycloalkylalkyloxy, amino, hydroxy, hydroxyalkyl, acyl, heteroaryl, heteroaryloxy, heteroarylalkyl, heteroarylalkoxy, aryloxyalkyl, aryloxyaryl, alkylamido, alkanoylamino, arylcarbonylamino, nitro, cyano, thiol, haloalkyl, trihaloalkyl and/or alkylthio, sulfonylaryl and/or any of the R$^1$ groups. Where particular substituted alkyl groups are identified herein they are named by adding the term "alkyl" at the end of the name of the substituent radical (e.g., aralkyl, heteroaralkyl etc.).

Unless otherwise indicated, the term "cycloalkyl" as employed herein alone or as part of another group includes saturated or partially unsaturated (containing 1 or more double bonds) cyclic hydrocarbon groups containing 1 to 3 rings, including monocyclicalkyl, bicyclicalkyl and tricyclicalkyl, containing a total of 3 to 20 carbons forming the rings, preferably 3 to 10 carbons, forming the ring and which may be fused to 1 or 2 aromatic rings as described for aryl, which include cyclopropyl, cyclobutyl, cyclopentyl, cyclohexyl, cycloheptyl, cyclooctyl, cyclodecyl and cyclododecyl, cyclohexenyl,

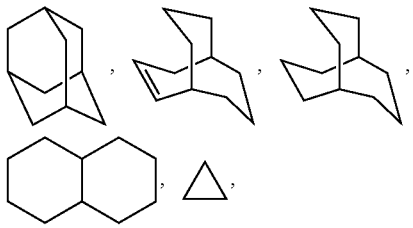

any of which groups may be optionally substituted with 1 to 4 substituents such as halogen, alkyl, alkoxy, hydroxy, aryl, aryloxy, arylalkyl, cycloalkyl, alkylamido, alkanoylamino, oxo, acyl, arylcarbonylamino, amino, nitro, cyano, thiol and/or alkylthio and/or any of the R$^1$ groups.

The term "cycloalkenyl" as employed herein alone or as part of another group refers to cyclic hydrocarbons containing 3 to 12 carbons, preferably 5 to 10 carbons and 1 or more double bonds. Exemplary cycloalkenyl groups include cyclopentenyl, cyclohexenyl, cycloheptenyl, cyclooctenyl, cyclohexadienyl, and cycloheptadienyl, which may be optionally substituted as defined for cycloalkyl.

The term "cycloalkylene" or "-(cycloalkyl)-" as employed herein refers to a "cycloalkyl" group which includes free bonds and thus is a linking group such as

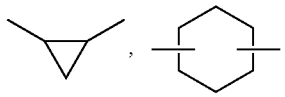

and the like, and may optionally be substituted as defined above for "cycloalkyl".

The term "alkanoyl" as used herein alone or as part of another group refers to alkyl linked to a carbonyl group.

Unless otherwise indicated, the term "lower alkenyl" or "alkenyl" as used herein by itself or as part of another group refers to straight or branched chain radicals of 2 to 20 carbons, preferably 2 to 12 carbons, and more preferably 1 to 8 carbons in the normal chain, which include one to six double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like, and which may be optionally substituted with 1 to 4 substituents, namely, halogen, haloalkyl, alkyl, alkoxy, alkenyl, alkynyl, aryl, arylalkyl, cycloalkyl, amino, hydroxy, heteroaryl, cycloheteroalkyl, alkanoylamino, alkylamido, arylcarbonyl-amino, nitro, cyano, thiol, alkylthio and/or any of the R$^1$ groups.

The terms "arylalkenyl" and "arylalkynyl" as used alone or as part of another group refer to alkenyl and alkynyl groups as described above having an aryl substituent.

Where alkyl groups as defined above have single bonds for attachment to other groups at two different carbon atoms, they are termed "alkylene" groups and may optionally be substituted as defined above for "alkyl".

Where alkenyl groups as defined above and alkynyl groups as defined above, respectively, have single bonds for attachment at two different carbon atoms, they are termed "alkenylene groups" and "alkynylene groups", respectively, and may optionally be substituted as defined above for "alkenyl" and "alkynyl".

Suitable alkylene, alkenylene or alkynylene groups $(CH_2)_x$ or $(CH_2)_y$ (where, y is 1 to 8, preferably 1 to 5, and x is 1 to 5, preferably 1 to 3, which includes alkylene, alkenylene or alkynylene groups) as defined herein, may optionally include 1, 2, or 3 substituents which include alkyl, alkenyl, halogen, cyano, hydroxy, alkoxy, amino, thioalkyl, keto, $C_3$–$C_6$ cycloalkyl, alkylcarbonylamino or alkylcarbonyloxy.

Examples of $(CH_2)_x$ or $(CH_2)_y$, alkylene, alkenylene and alkynylene include

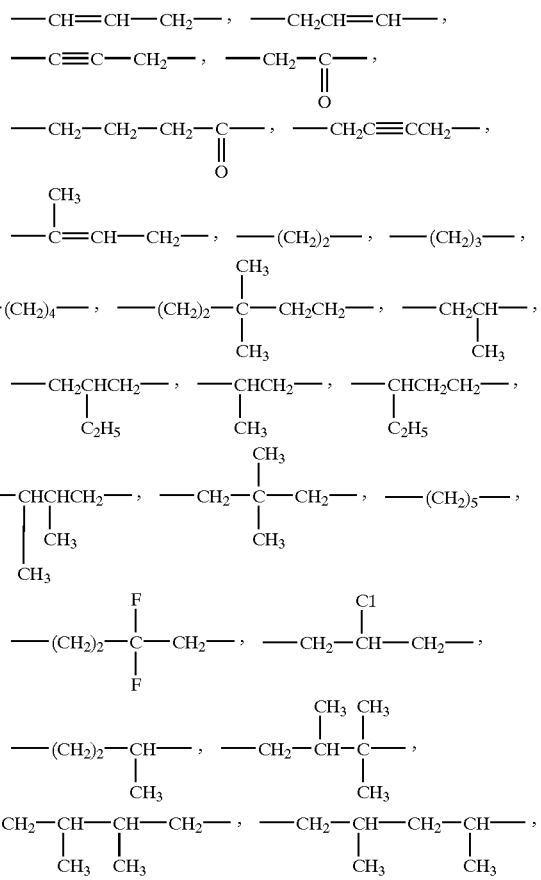

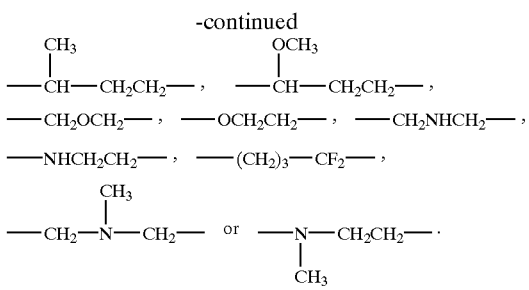

The term "halogen" or "halo" as used herein alone or as part of another group refers to chlorine, bromine, fluorine, and iodine as well as $CF_3$, with chlorine, bromine or fluorine being preferred.

The term "metal ion" refers to alkali metal ions such as sodium, potassium or lithium and alkaline earth metal ions such as magnesium and calcium, as well as zinc and aluminum.

Unless otherwise indicated, the terms "aryl" or "ar" as employed herein alone or as part of another group refers to monocyclic and bicyclic aromatic groups containing 6 to 10 carbons in the ring portion (such as phenyl or naphthyl including 1-naphthyl and 2-naphthyl) and may optionally include one to three additional rings fused to a carbocyclic ring or a heterocyclic ring (such as aryl, cycloalkyl, heteroaryl or cycloheteroalkyl rings for example

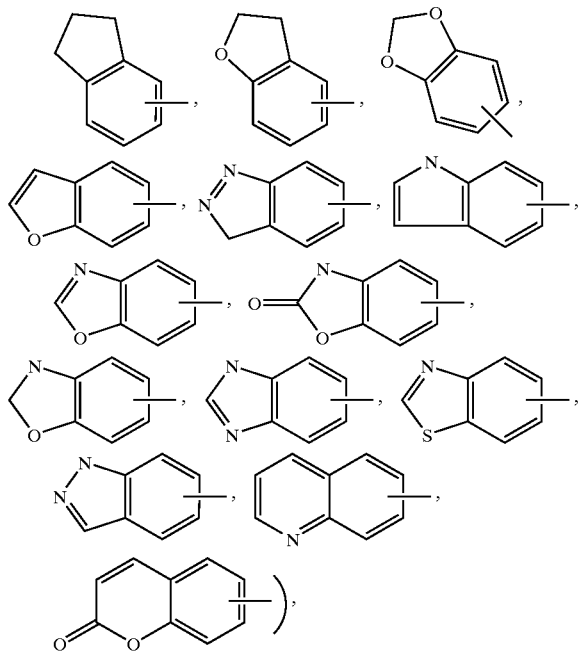

and may be optionally substituted through available carbon atoms with 1, 2, or 3 groups selected from hydrogen, halo, haloalkyl, alkyl, substituted alkyl, alkoxy, haloalkoxy, alkenyl, trifluoromethyl, trifluoromethoxy, alkynyl, cycloalkyl, cycloalkyl-alkyl, cycloheteroalkyl, cycloheteroalkylalkyl, aryl, substituted aryl, heteroaryl, substituted heteroaryl, arylalkyl, aryloxy, aryloxyalkyl, arylalkoxy, arylthio, arylazo, heteroarylalkyl, heteroarylalkenyl, heteroarylheteroaryl, heteroaryloxy, hydroxy, nitro, cyano, amino, substituted amino wherein the amino includes 1 or 2 substituents (which are alkyl, aryl or any of the other aryl compounds mentioned in the definitions), thiol, alkylthio, arylthio, heteroarylthio, arylthioalkyl, alkoxyarylthio, alkylcarbonyl, arylcarbonyl, alkyl-aminocarbonyl, arylaminocarbonyl, alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino or arylsulfonylaminocarbonyl, sulfonylaryl, sulfonylarylalkyl, and/or any of the $R^1$ groups.

Unless otherwise indicated, the term "lower alkoxy", "alkoxy", "aryloxy" or "aralkoxy" as employed herein alone or as part of another group includes any of the above alkyl, aralkyl or aryl groups linked to an oxygen atom.

Unless otherwise indicated, the term "substituted amino" as employed herein alone or as part of another group refers to amino substituted with one or two substituents, which may be the same or different, such as alkyl, aryl, arylalkyl, heteroaryl, heteroarylalkyl, cycloheteroalkyl, cycloheteroalkylalkyl, cycloalkyl, cycloalkylalkyl, haloalkyl, hydroxyalkyl, alkoxyalkyl or thioalkyl. In addition, the amino substituents may be taken together with the nitrogen atom to which they are attached to form 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl-1-piperazinyl, 4-diarylalkyl-1-piperazinyl, 1-pyrrolidinyl, 1-piperidinyl, or 1-azepinyl, optionally substituted with alkyl, alkoxy, alkylthio, halo, trifluoromethyl or hydroxy.

Unless otherwise indicated, the term "lower alkylthio", "alkylthio", "arylthio" or "aralkylthio" as employed herein alone or as part of another group includes any of the above alkyl, aralkyl or aryl groups linked to a sulfur atom.

Unless otherwise indicated, the term "lower alkylamino", "alkylamino", "arylamino", or "arylalkylamino" as employed herein alone or as part of another group includes any of the above alkyl, aryl or arylalkyl groups linked to a nitrogen atom.

Unless otherwise indicated, the term "acyl" as employed herein by itself or part of another group, as defined herein, refers to an organic radical linked to a carbonyl group

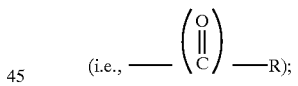

examples of acyl groups include any of the $R^1$ groups attached to a carbonyl, such as alkanoyl, alkenoyl, aroyl, aralkanoyl, heteroaroyl, cycloalkanoyl, cycloheteroalkanoyl and the like. Such groups may also be identified by adding the term "carbonyl" at the end of the name of the organic radical R bonded to the acyl group (e.g., alkylaminocarbonyl, alkoxycarbonyl, etc).

Unless otherwise indicated, the term "cycloheteroalkyl" as used herein alone or as part of another group refers to a 5-, 6- or 7-membered saturated or partially unsaturated ring which includes 1 or more hetero atoms such as nitrogen, oxygen and/or sulfur, linked through a carbon atom or a heteroatom, where possible, optionally via the linker $(CH_2)_x$, such as

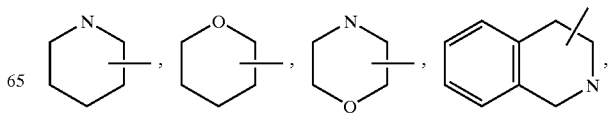

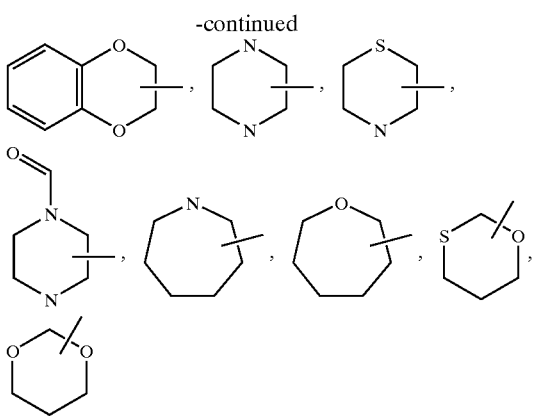

and the like. The above groups may include 1 to 4 substituents such as alkyl, halo, oxo and/or any of the $R^1$ groups. In addition, any of the cycloheteroalkyl rings can be fused to a cycloalkyl, aryl, heteroaryl or cycloheteroalkyl ring.

Unless otherwise indicated, the term "heteroaryl" as used herein alone or as part of another group refers to monocyclic and bicyclic aromatic rings containing from 5 to 10 atoms, which includes 1, 2, 3 or 4 hetero atoms such as nitrogen, oxygen or sulfur, and such rings fused to an aryl, cycloalkyl, heteroaryl or cycloheteroalkyl ring (e.g. benzothiophenyl, indolyl), where the nitrogen and sulfur heteroatoms may optionally be oxidized and the nitrogen heteroatoms may optionally be quaternized. The heteroaryl group may optionally include 1 to 4 substituents such as any of the $R^1$ groups. Examples of heteroaryl groups include the following:

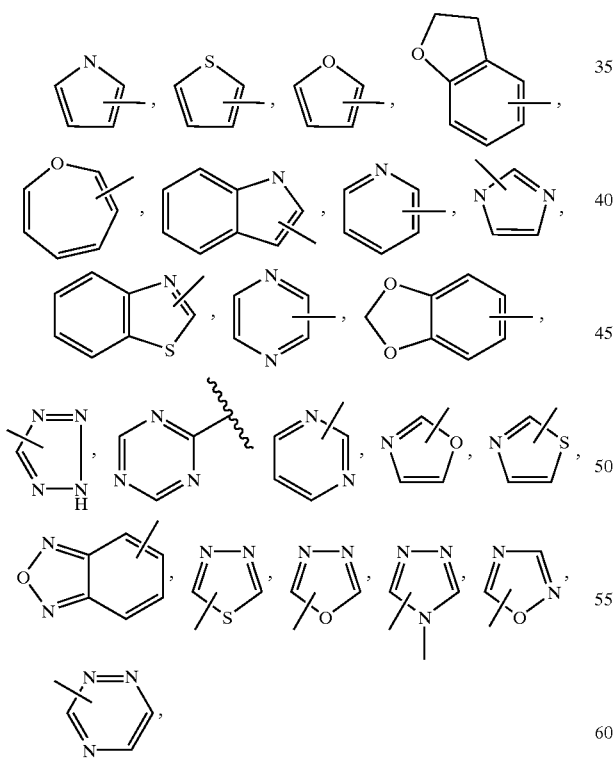

and the like.

The term "cycloheteroalkylalkyl" as used herein alone or as part of another group refers to cycloheteroalkyl groups as defined above linked through a C atom or heteroatom to a $(CH_2)_x$ chain.

The term "heteroarylalkyl" or "heteroarylalkenyl" as used herein alone or as part of another group refers to a heteroaryl group as defined above linked through a C atom or heteroatom to a $-(CH_2)_x-$ chain, alkylene or alkenylene as defined above.

The term "polyhaloalkyl" as used herein refers to an "alkyl" group as defined above which includes from 2 to 9, preferably from 2 to 5, halo substituents, such as F or Cl, preferably F, such as $CF_3CH_2$, $CF_3$ or $CF_3CF_2CH_2$.

The term "polyhaloalkyloxy" as used herein refers to an "alkoxy" or "alkyloxy" group as defined above which includes from 2 to 9, preferably from 2 to 5, halo substituents, such as F or Cl, preferably F, such as $CF_3CH_2O$, $CF_3O$ or $CF_3CF_2CH_2O$.

The term "prodrug esters" as employed herein includes prodrug esters which are known in the art for carboxylic acids such as similar carboxylic acid esters such as methyl, ethyl benzyl and the like. Other examples include the following groups: (1-alkanoyloxy)alkyl such as,

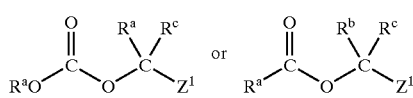

wherein $R^a$, $R^b$ and $R^c$ are H, alkyl, aryl or aryl-alkyl; however $R^aO$ cannot be HO, and where $Z^1$ is

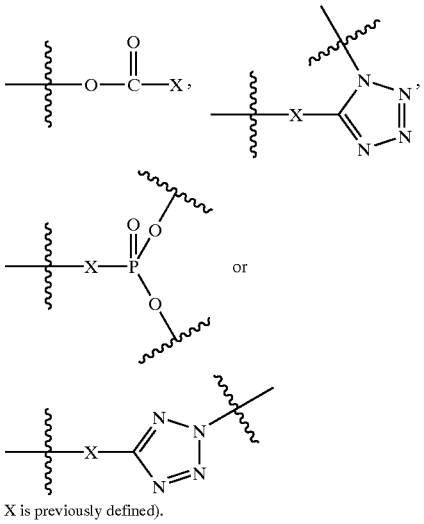

(where X is previously defined).

Examples of such prodrug esters include

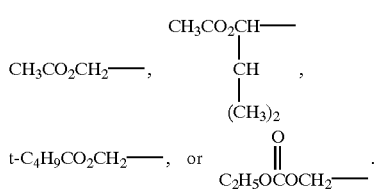

Other examples of suitable prodrug esters include

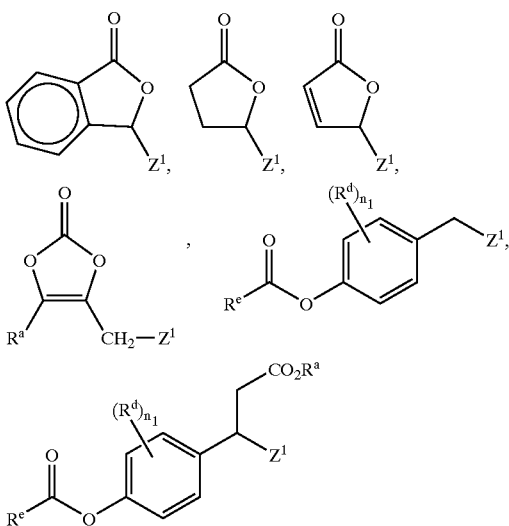

wherein $R^a$ can be H, alkyl (such as methyl or t-butyl), arylalkyl (such as benzyl) or aryl (such as phenyl); $R^d$ is H, alkyl, halogen or alkoxy, $R^e$ is alkyl, aryl, arylalkyl or alkoxyl, and $n_1$ is 0, 1 or 2.

The compounds of formula I form salts which are also within the scope of this invention. Reference to a compound of the formula I herein is understood to include reference to salts thereof, unless otherwise indicated. The term "salt(s)", as employed herein, denotes acidic and/or basic salts formed with inorganic and/or organic acids and bases. In addition, when a compound of formula I contains a both a basic moiety and an acidic moiety, zwitterions ("inner salts") may be formed and are included within the term "salt(s)" as used herein. Pharmaceutically acceptable (i.e., non-toxic, physiologically acceptable) salts are preferred, although other salts are also useful, e.g., in isolation or purification steps which may be employed during preparation. Salts of the compounds of the formula I may be formed, for example, by reacting a compound I with an amount of acid or base, such as an equivalent amount, in a medium such as one in which the salt precipitates or in an aqueous medium followed by lyophilization.

The compounds of formula I which contain a basic moiety may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, herisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

The compounds of formula I which contain an acidic moiety may form salts with a variety of organic and inorganic bases. Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines (formed with N,N-bis(dehydroabietyl) ethylenediamine), N-methyl-D-glucamines, N-methyl-D-glucamides, t-butyl amines, and salts with amino acids such as arginine, lysine and the like.

Prodrugs and solvates of the compounds of the invention are also contemplated herein. The term "prodrug", as employed herein, denotes a compound which, upon administration to a subject, undergoes chemical conversion by metabolic or chemical processes to yield a compound of the formula I, or a salt and/or solvate thereof. Solvates of the compounds of formula I are preferably hydrates.

To the extent that compounds of the formula I, and salts thereof, may exist in their tautomeric form, all such tautomeric forms are contemplated herein as part of the present invention.

All stereoisomers of the present compounds, such as those which may exist due to asymmetric carbons on the various substituents, including enantiomeric forms (which may exist even in the absence of asymmetric carbons) and diastereomeric forms, are contemplated within the scope of this invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. When diastereomeric or enantiomeric products are prepared, they can be separated by conventional methods for example, chromatographic or fractional crystallization.

Where desired, the compounds of structure I may be used in combination with one or more other types of therapeutic agents which may be administered orally in the same dosage form, in a separate oral dosage form or by injection.

The other type of therapeutic agent which may be optionally employed in combination with the aP2 inhibitor of formula I may be 1, 2, 3 or more antidiabetic agents or antihyperglycemic agents including insulin secretagogues or insulin sensitizers, or other antidiabetic agents preferably having a mechanism of action different from aP2 inhibition and may include biguanides, sulfonyl ureas, glucosidase inhibitors, glycogen phosphorylase inhibitors, PPAR γ agonists, such as thiazolidinediones, SGLT2 inhibitors, PPAR α/γ dual agonists, dipeptidyl peptidase IV (DP4) inhibitors, and/or meglitinides, as well as insulin, and/or glucagon-like peptide-1 (GLP-1).

It is believed that the use of the compounds of structure I in combination with another antidiabetic agent produces antihyperglycemic results greater than that possible from each of these medicaments alone and greater than the combined additive anti-hyperglycemic effects produced by these medicaments.

The other antidiabetic agent may be an oral antihyperglycemic agent preferably a biguanide such as metformin or phenformin or salts thereof, preferably metformin HCl.

Where the other antidiabetic agent is a biguanide, the compounds of structure I will be employed in a weight ratio to biguanide within the range from about 0.01:1 to about 100:1, preferably from about 0.1:1 to about 5:1.

The other antidiabetic agent may also preferably be a sulfonyl urea such as glyburide (also known as glibenclamide), glimepiride (disclosed in U.S. Pat. No. 4,379,785), glipizide, gliclazide or chlorpropamide, other known sulfonylureas or other antihyperglycemic agents which act on the ATP-dependent channel of the β-cells, with glyburide and glipizide being preferred, which may be administered in the same or in separate oral dosage forms.

The compounds of structure I will be employed in a weight ratio to the sulfonyl urea in the range from about 0.01:1 to about 100:1, preferably from about 0.2:1 to about 10:1.

The oral antidiabetic agent may also be a glucosidase inhibitor such as acarbose (disclosed in U.S. Pat. No. 4,904,769) or miglitol (disclosed in U.S. Patent No. 4,639,436), which may be administered in the same or in a separate oral dosage forms.

The compounds of structure I will be employed in a weight ratio to the glucosidase inhibitor within the range from about 0.01:1 to about 100:1, preferably from about 0.5:1 to about 50:1.

The compounds of structure I may be employed in combination with a PPAR γ agonist such as a thiazolidinedione oral anti-diabetic agent or other insulin sensitizers (which has an insulin sensitivity effect in NIDDM patients) such as troglitazone (Warner-Lambert's Rezulin®, disclosed in U.S. Pat. No. 4,572,912), rosiglitazone (SKB), pioglitazone (Takeda), Mitsubishi's MCC-555 (disclosed in U.S. Pat. No. 5,594,016), Glaxo-Welcome's GL-262570, englitazone (CP-68722, Pfizer) or darglitazone (CP-86325, Pfizer), isaglitazone (MIT/J&J), JTT-501 (JPNT/P&U), L-895645 (Merck), R-119702 (Sankyo/WL), NN-2344 (Dr. Reddy/NN), or YM-440 (Yamanouchi), preferably rosiglitazone and pioglitazone.

The compounds of structure I will be employed in a weight ratio to the thiazolidinedione in an amount within the range from about 0.01:1 to about 100:1, preferably from about 0.1:1 to about 10:1.

The sulfonyl urea and insulin sensitizer in amounts of less than about 150 mg oral antidiabetic agent may be incorporated in a single tablet with the compounds of structure I.

The compounds of structure I may also be employed in combination with a antihyperglycemic agent such as insulin or with glucagon-like peptide-1 (GLP-1) such as GLP-1 (1–36) amide, GLP-1(7–36) amide, GLP-1(7–37) (as disclosed in U.S. Pat. No. 5,614,492 to Habener, the disclosure of which is incorporated herein by reference), as well as AC2993 (Amylen) and LY-315902 (Lilly), which may be administered via injection, intranasal, or by transdermal or buccal devices.

Where present, metformin, the sulfonyl ureas, such as glyburide, glimepiride, glipyride, glipizide, chlorpropamide and gliclazide and the glucosidase inhibitors acarbose or miglitol or insulin (injectable, pulmonary, buccal, or oral) may be employed in formulations as described above and in amounts and dosing as indicated in the Physician's Desk Reference (PDR).

Where present, metformin or salt thereof may be employed in amounts within the range from about 500 to about 2000 mg per day which may be administered in single or divided doses one to four times daily.

Where present, the thiazolidinedione anti-diabetic agent may be employed in amounts within the range from about 0.01 to about 2000 mg/day which may be administered in single or divided doses one to four times per day.

Where present insulin may be employed in formulations, amounts and dosing as indicated by the Physician's Desk Reference.

Where present GLP-1 peptides may be administered in oral buccal formulations, by nasal administration or parenterally as described in U.S. Pat. Nos. 5,346,701 (TheraTech), 5,614,492 and 5,631,224 which are incorporated herein by reference.

The other antidiabetic agent may also be a PPAR α/γ dual agonist such as AR-HO39242 (Astra/Zeneca), GW-409544 (Glaxo-Wellcome), KRP297 (Kyorin Merck) as well as those disclosed by Murakami et al, "A Novel Insulin Sensitizer Acts As a Coligand for Peroxisome Proliferation—Activated Receptor Alpha (PPAR alpha) and PPAR gamma. Effect on PPAR alpha Activation on Abnormal Lipid Metabolism in Liver of Zucker Fatty Rats", Diabetes 47, 1841–1847 (1998), and in U.S. provisional application No. 60/155,400, filed Sep. 22, 1999, (attorney file LA29) the disclosure of which is incorporated herein by reference, employing dosages as set out therein, which compounds designated as preferred are preferred for use herein.

The other antidiabetic agent may be an SGLT2 inhibitor such as disclosed in U.S. provisional application No. 60/158,773, filed Oct. 12, 1999 (attorney file LA49), employing dosages as set out herein. Preferred are the compounds designated as preferred in the above application.

The other antidiabetic agent may be a DP4 inhibitor such as disclosed in WO99/38501, WO99/46272, WO99/67279 (PROBIODRUG), WO99/67278 (PROBIODRUG), WO99/61431 (PROBIODRUG), NVP-DPP728A (1-[[[2-[(5-cyanopyridin-2-yl)amino]ethyl]amino]acetyl]-2-cyano-(S)-pyrrolidine) (Novartis) (preferred) as disclosed by Hughes et al, Biochemistry, 38(36), 11597–11603, 1999, TSL-225 (tryptophyl-1,2,3,4-tetrahydroisoquinoline-3-carboxylic acid (disclosed by Yamada et al, Bioorg. & Med. Chem. Lett. 8 (1998) 1537–1540, 2-cyanopyrrolidides and 4-cyanopyrrolidides as disclosed by Ashworth et al, Bioorg. & Med. Chem. Lett., Vol. 6, No. 22, pp 1163–1166 and 2745–2748 (1996) employing dosages as set out in the above references.

The meglitinide which may optionally be employed in combination with the compound of formula I of the invention may be repaglinide, nateglinide (Novartis) or KAD1229 (PF/Kissei), with repaglinide being preferred.

The aP2 inhibitor of formula I will be employed in a weight ratio to the meglitinide, PPAR γ agonist, PPAR α/γ dual agonist, SGLT2 inhibitor or DP4 inhibitor within the range from about 0.01:1 to about 100:1, preferably from about 0.2:1 to about 10:1.

The hypolipidemic agent or lipid-lowering agent which may be optionally employed in combination with the compounds of formula I of the invention may include 1, 2, 3 or more MTP inhibitors, HMG CoA reductase inhibitors, squalene synthetase inhibitors, fibric acid derivatives, ACAT inhibitors, lipoxygenase inhibitors, cholesterol absorption inhibitors, ileal $Na^+$/bile acid cotransporter inhibitors, upregulators of LDL receptor activity, bile acid sequestrants, and/or nicotinic acid and derivatives thereof.

MTP inhibitors employed herein include MTP inhibitors disclosed in U.S. Pat. No. 5,595,872, U.S. Pat. No. 5,739,135, U.S. Pat. No. 5,712,279, U.S. Pat. No. 5,760,246, U.S. Pat. No. 5,827,875, U.S. Pat. No. 5,885,983 and U.S. application Ser. No. 09/175,180 filed Oct. 20, 1998, now U.S. Pat. No. 5,962,440. Preferred are each of the preferred MTP inhibitors disclosed in each of the above patents and applications.

All of the above U.S. Patents and applications are incorporated herein by reference.

Most preferred MTP inhibitors to be employed in accordance with the present invention include preferred MTP inhibitors as set out in U.S. Pat. Nos. 5,739,135 and 5,712,279, and U.S. Pat. No. 5,760,246.

The most preferred MTP inhibitor is 9-[4-[4-[[2-(2,2,2-Trifluoroethoxy)benzoyl]amino]-1-piperidinyl]butyl]-N-(2,2,2-trifluoroethyl)-9H-fluorene-9-carboxamide

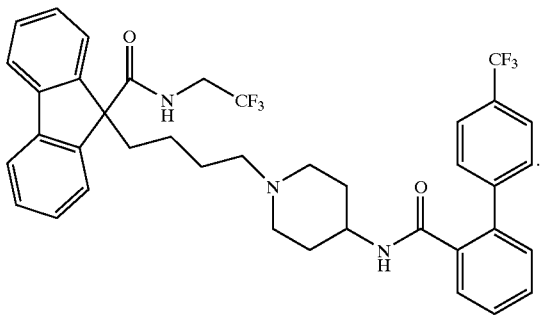

The hypolipidemic agent may be an HMG CoA reductase inhibitor which includes, but is not limited to, mevastatin and related compounds as disclosed in U.S. Pat. No. 3,983,140, lovastatin (mevinolin) and related compounds as disclosed in U.S. Pat. No. 4,231,938, pravastatin and related compounds such as disclosed in U.S. Pat. No. 4,346,227, simvastatin and related compounds as disclosed in U.S. Pat. Nos. 4,448,784 and 4,450,171. Other HMG CoA reductase inhibitors which may be employed herein include, but are not limited to, fluvastatin, disclosed in U.S. Pat. No. 5,354,772, cerivastatin disclosed in U.S. Pat. Nos. 5,006,530 and 5,177,080, atorvastatin disclosed in U.S. Pat. Nos. 4,681,893, 5,273,995, 5,385,929 and 5,686,104, atavastatin (Nissan/Sankyo's nisvastatin (NK-104)) disclosed in U.S. Pat. No. 5,011,930, Shionogi-Astra/Zeneca visastatin (ZD-4522) disclosed in U.S. Pat. No. 5,260,440, and related statin compounds disclosed in U.S. Pat. No. 5,753,675, pyrazole analogs of mevalonolactone derivatives as disclosed in U.S. Pat. No. 4,613,610, indene analogs of mevalonolactone derivatives as disclosed in PCT application WO 86/03488, 6-[2-(substituted-pyrrol-1-yl)-alkyl]pyran-2-ones and derivatives thereof as disclosed in U.S. Pat. No. 4,647,576, Searle's SC-45355 (a 3-substituted pentanedioic acid derivative) dichloroacetate, imidazole analogs of mevalonolactone as disclosed in PCT application WO 86/07054, 3-carboxy-2-hydroxy-propane-phosphonic acid derivatives as disclosed in French Patent No. 2,596,393, 2,3-disubstituted pyrrole, furan and thiophene derivatives as disclosed in European Patent Application No. 0221025, naphthyl analogs of mevalonolactone as disclosed in U.S. Pat. No. 4,686,237, octahydronaphthalenes such as disclosed in U.S. Pat. No. 4,499,289, keto analogs of mevinolin (lovastatin) as disclosed in European Patent Application No.0,142,146 A2, and quinoline and pyridine derivatives disclosed in U.S. Pat. Nos. 5,506,219 and 5,691,322.

In addition, phosphinic acid compounds useful in inhibiting HMG CoA reductase suitable for use herein are disclosed in GB 2205837.

The squalene synthetase inhibitors suitable for use herein include, but are not limited to, α-phosphono-sulfonates disclosed in U.S. Pat. No. 5,712,396, those disclosed by Biller et al, J. Med. Chem., 1988, Vol. 31, No. 10, pp 1869–1871, including isoprenoid (phosphinyl-methyl) phosphonates as well as other known squalene synthetase inhibitors, for example, as disclosed in U.S. Pat. Nos. 4,871,721 and 4,924,024 and in Biller, S. A., Neuenschwander, K., Ponpipom, M. M., and Poulter, C. D., Current Pharmaceutical Design, 2, 1-40 (1996).

In addition, other squalene synthetase inhibitors suitable for use herein include the terpenoid pyrophosphates disclosed by P. Ortiz de Montellano et al, J. Med. Chem., 1977, 20, 243–249, the farnesyl diphosphate analog A and presqualene pyrophosphate (PSQ-PP) analogs as disclosed by Corey and Volante, J. Am. Chem. Soc., 1976, 98, 1291–1293, phosphinylphosphonates reported by McClard, R. W. et al, J.A.C.S., 1987, 109, 5544 and cyclopropanes reported by Capson, T. L., PhD dissertation, June, 1987, Dept. Med. Chem. U of Utah, Abstract, Table of Contents, pp 16, 17, 4043, 48–51, Summary.

Other hypolipidemic agents suitable for use herein include, but are not limited to, fibric acid derivatives, such as fenofibrate, gemfibrozil, clofibrate, bezafibrate, ciprofibrate, clinofibrate and the like, probucol, and related compounds as disclosed in U.S. Pat. No. 3,674,836, probucol and gemfibrozil being preferred, bile acid sequestrants such as cholestyramine, colestipol and DEAE-Sephadex (Secholex®, Policexide®), as well as lipostabil (Rhone-Poulenc), Eisai E-5050 (an N-substituted ethanolamine derivative), imanixil (HOE-402), tetrahydrolipstatin (THL), istigmastanylphos-phorylcholine (SPC, Roche), aminocyclodextrin (Tanabe Seiyoku), Ajinomoto AJ-814 (azulene derivative), melinamide (Sumitomo), Sandoz 58-035, American Cyanamid CL-277,082 and CL-283,546 (disubstituted urea derivatives), nicotinic acid, acipimox, acifran, neomycin, p-aminosalicylic acid, aspirin, poly (diallylmethylamine) derivatives such as disclosed in U.S. Pat. No. 4,759,923, quaternary amine poly (diallyldimethylammonium chloride) and ionenes such as disclosed in U.S. Pat. No. 4,027,009, and other known serum cholesterol lowering agents.

The other hypolipidemic agent may be an ACAT inhibitor such as disclosed in, Drugs of the Future 24, 9–15 (1999), (Avasimibe); "The ACAT inhibitor, C1-1011 is effective in the prevention and regression of aortic fatty streak area in hamsters", Nicolosi et al, Atherosclerosis (Shannon, frel). (1998), 137(1), 77–85; "The pharmacological profile of FCE 27677: a novel ACAT inhibitor with potent hypolipidemic activity mediated by selective suppression of the hepatic secretion of ApoB 100-containing lipoprotein", Ghiselli, Giancarlo, Cardiovasc. Drug Rev. (1998), 16(1), 16–30; "RP 73163: a bioavailable alkylsulfinyl-diphenylimidazole ACAT inhibitor", Smith, C., et al, Bioorg. Med. Chem. Lett. (1996), 6(1), 47–50; "ACAT inhibitors: physiologic mechanisms for hypolipidemic and anti-atherosclerotic activities in experimental animals", Krause et al, Editor(s): Ruffolo, Robert R., Jr.; Hollinger, Mannfred A., Inflammation: Mediators Pathways (1995), 173–98, Publisher: CRC, Boca Raton, Fla.; "ACAT inhibitors: potential anti-atherosclerotic agents", Sliskovic et al, Curr. Med. Chem. (1994), 1(3), 204–25; "Inhibitors of acyl-CoA:cholesterol O-acyl transferase (ACAT) as hypocholesterolemic agents. 6. The first water-soluble ACAT inhibitor with lipid-regulating activity. Inhibitors of acyl-CoA:cholesterol acyltransferase (ACAT). 7. Development of a series of substituted N-phenyl-N'-[(1-phenylcyclopentyl)methyl]ureas with enhanced hypocholesterolemic activity", Stout et al, Chemtracts: Org. Chem. (1995), 8(6), 359–62, or TS-962 (Taisho Pharmaceutical Co. Ltd).

The hypolipidemic agent may be an upregulator of LD2 receptor activity such as MD-700 (Taisho Pharmaceutical Co. Ltd) and LY295427 (Eli Lilly).

The hypolipidemic agent may be a cholesterol absorption inhibitor preferably Schering-Plough's SCH48461 as well as those disclosed in Atherosclerosis 115, 45–63 (1995) and J. Med. Chem. 41, 973 (1998).

The hypolipidemic agent may be an ileal $Na^+$/bile acid cotransporter inhibitor such as disclosed in Drugs of the Future, 24, 425–430 (1999).

Preferred hypolipidemic agents are pravastatin, lovastatin, simvastatin, atorvastatin, fluvastatin, cerivastatin, atavastatin and ZD4522.

The above-mentioned U.S. patents are incorporated herein by reference. The amounts and dosages employed will be as indicated in the Physician's Desk Reference and/or in the patents set out above.

The compounds of formula I of the invention will be employed in a weight ratio to the hypolipidemic agent (were present), within the range from about 500:1 to about 1:500, preferably from about 100:1 to about 1:100.

The dose administered must be carefully adjusted according to age, weight and condition of the patient, as well as the route of administration, dosage form and regimen and the desired result.

The dosages and formulations for the hypolipidemic agent will be as disclosed in the various patents and applications discussed above.

The dosages and formulations for the other hypolipidemic agent to be employed, where applicable, will be as set out in the latest edition of the Physicians' Desk Reference.

For oral administration, a satisfactory result may be obtained employing the MTP inhibitor in an amount within the range of from about 0.01 mg/kg to about 500 mg and preferably from about 0.1 mg to about 100 mg, one to four times daily.

A preferred oral dosage form, such as tablets or capsules, will contain the MTP inhibitor in an amount of from about 1 to about 500 mg, preferably from about 2 to about 400 mg, and more preferably from about 5 to about 250 mg, one to four times daily.

For oral administration, a satisfactory result may be obtained employing an HMG CoA reductase inhibitor, for example, pravastatin, lovastatin, simvastatin, atorvastatin, fluvastatin or cerivastatin in dosages employed as indicated in the Physician's Desk Reference, such as in an amount within the range of from about 1 to 2000 mg, and preferably from about 4 to about 200 mg.

The squalene synthetase inhibitor may be employed in dosages in an amount within the range of from about 10 mg to about 2000 mg and preferably from about 25 mg to about 200 mg.

A preferred oral dosage form, such as tablets or capsules, will contain the HMG CoA reductase inhibitor in an amount from about 0.1 to about 100 mg, preferably from about 5 to about 80 mg, and more preferably from about 10 to about 40 mg.

A preferred oral dosage form, such as tablets or capsules will contain the squalene synthetase inhibitor in an amount of from about 10 to about 500 mg, preferably from about 25 to about 200 mg.

The other hypolipidemic agent may also be a lipoxygenase inhibitor including a 15-lipoxygenase (15-LO) inhibitor such as benzimidazole derivatives as disclosed in WO 97/12615, 15-LO inhibitors as disclosed in WO 97/12613, isothiazolones as disclosed in WO 96/38144, and 15-LO inhibitors as disclosed by Sendobry et al "Attenuation of diet-induced atherosclerosis in rabbits with a highly selective 15-lipoxygenase inhibitor lacking significant antioxidant properties, Brit. J. Pharmacology (1997) 120, 1199–1206, and Cornicelli et al, "15-Lipoxygenase and its Inhibition: A Novel Therapeutic Target for Vascular Disease", Current Pharmaceutical Design, 1999, 5, 11–20.

The compounds of formula I and the hypolipidemic agent may be employed together in the same oral dosage form or in separate oral dosage forms taken at the same time.

The compositions described above may be administered in the dosage forms as described above in single or divided doses of one to four times daily. It may be advisable to start a patient on a low dose combination and work up gradually to a high dose combination.

The preferred hypolipidemic agent is pravastatin, simvastatin, lovastatin, atorvastatin, fluvastatin or cerivastatin.

The other type of therapeutic agent which may be optionally employed with the aP2 inhibitor of formula I may be 1, 2, 3 or more of an anti-obesity agent including a beta 3 adrenergic agonist, a lipase inhibitor, a serotonin (and dopamine) reuptake inhibitor, a thyroid receptor beta drug and/or an anorectic agent.

The beta 3 adrenergic agonist which may be optionally employed in combination with a compound of formula I may be AJ9677 (Takeda/Dainippon), L750355 (Merck), or CP331648 (Pfizer) or other known beta 3 agonists as disclosed in U.S. Pat. Nos. 5,541,204, 5,770,615, 5,491,134, 5,776,983 and 5,488,064, with AJ9677, L750,355 and CP331648 being preferred.

The lipase inhibitor which may be optionally employed in combination with a compound of formula I may be orlistat or ATL-962 (Alizyme), with orlistat being preferred.

The serotonin (and dopoamine) reuptake inhibitor which may be optionally employed in combination with a compound of formula I may be sibutramine, topiramate (Johnson & Johnson) or axokine (Regeneron), with sibutramine and topiramate being preferred.

The thyroid receptor beta compound which may be optionally employed in combination with a compound of formula I may be a thyroid receptor ligand as disclosed in WO97/21993 (U. Cal SF), WO99/00353 (KaroBio) and GB98/284425 (KaroBio), with compounds of the KaroBio applications being preferred.

The anorectic agent which may be optionally employed in combination with a compound of formula I may be dexamphetamine, phentermine, phenylpropanolamine or mazindol, with dexamphetamine being preferred.

The various anti-obesity agents described above may be employed in the same dosage form with the compound of formula I or in different dosage forms, in dosages and regimens as generally known in the art or in the PDR.

The other type of therapeutic agent which may be optionally employed with the aP2 inhibitor of formula I may be 1, 2, 3 or more of an antihypertensive agent including an ACE inhibitor, a vasopeptidase inhibitor, an angiotensin In antagonist, a calcium channel blocker, a potassium channel opener, an alpha-blocker, a beta blocker, a centrally acting alpha agonist, and/or a diuretic.

The ACE inhibitor which may be optionally employed in combination with a compound of formula I may be lisinopril, enalapril, quinapril, benazepril, fosinopril, fentiapril, ramipril, captopril, enalaprilat, moexipril, tranolapril, perindopril, ceranopril, zofenopril or cetapril.

Preferred ACE inhibitors are captopril, as well as fosinopril, enalapril, lisinopril, quinapril, benazepril, fentiapril, ramipril, and moexipril.

The vasopeptidase inhibitor (also known as NEP/ACE inhibitors) which may be optionally employed with the aP2 inhibitor of formula I may be omapatrilat (most preferred) and [S-(R*,R*)]-hexahydro-6-[(2-mercapto-1-oxo-3-phenylpropyl)amino]-2,2-dimethyl-7-oxo-1H-azepine-1-acetic acid (BMS 189,921 also preferred), as well as those disclosed in U.S. Pat. Nos. 5,362,727, 5,366,973, 5,225,401, 4,722,810, 5,223,516, 4,749,688. U.S. Pat. No. 5,504,080, U.S. Pat. No. 5,552,397, U.S. Pat. No. 5,612,359, U.S. Pat. No. 5,525,723, European Patent Application 0599,444, 0481,522, 0599,444, 0595,610, European Patent Application 0534363.A2, 534,396 and 534,492, and European Patent Application 0629627.A2.

Preferred are those NEP/ACE inhibitors which are designated as preferred in the above patents/applications which U.S. patents/applications are incorporated herein by reference.

The angiotensin II receptor antagonist (also referred to herein as angiotensin antagonist or AII antagonist) which may be optionally employed in combination with a compound of formula I may be irbesartan, losartan, valsartan, candesartan, telmisartan, tasosartan and/or eprosartan, with irbesartan or losartan being preferred.

The calcium channel blocker (also referred to as a calcium antagonist) which may be optionally employed in combination with a compound of formula I may be amlodipine, diltiazem, nifedipine, verapamil, feldodipine, nisoldipine, isradipine and/or nicardipine, with amlodipine, diltiazem, verapamil and nifedipine being preferred.

The alpha-blocker which may be optionally employed in combination with a compound of formula I may be terazosin, doxazosin or prazosin, all of which are preferred.

The beta-blocker which may be optionally employed in combination with a compound of formula I may be nadolol, atenolol, propranolol, metoprolol, carvediol or sotalol, with atenolol and nadolol being preferred.

The potassium channel opener which may be optionally employed in combination with a compound of formula I may be minoxidil.

The centrally acting $\alpha$ agonist antihypertensive agent which may be optionally employed in combination with a compound of formula I may be clonidine or guanfacine, with clonidine being preferred.

The diuretic which may be optionally employed in connection with a compound of formula I may be hydrochlorothiazide, torasemide, furosemide, spironolactone and/or indapamide, with hydrochlorothiazide and furosemide being preferred.

The antiplatelet agent (also known as platelet aggregation inhibitor) which may be optionally employed in combination with a compound of formula I may be aspirin, clopidogrel, ticlopidine, dipyridamole, abciximab, tirofiban, eptifibatide, anagrelide and/or ifetroban, with aspirin and clopidogrel being preferred.

The anti-infective agent which may be optionally employed in combination with a compound of formula I may be an anti-infective that is effective against chlamydial infections, such as azithromycin, gatifloxacin, ciprofloxacin, levofloxacin and trovafloxacin, with azithromycin and gatifloxacin being preferred.

The various antihypertensive agents and antiplatelet agents and anti-infective agents described above may be employed in the same dosage form with the compound of formula I or in different dosage forms, in dosages and regimens as generally known in the art or in the PDR.

In carrying our the method of the invention, a pharmaceutical composition will be employed containing the compounds of structure I, with or without another therapeutic agent, in association with a pharmaceutical vehicle or diluent. The pharmaceutical composition can be formulated employing conventional solid or liquid vehicles or diluents and pharmaceutical additives of a type appropriate to the mode of desired administration. The compounds can be administered to mammalian species including humans, monkeys, dogs, etc. by an oral route, for example, in the form of tablets, capsules, granules or powders, or they can be administered by a parenteral route in the form of injectable preparations. The dose for adults is preferably between 20 and 2,000 mg per day, which can be administered in a single dose or in the form of individual doses from 14 times per day.

A typical capsule for oral administration contains compounds of structure I (250 mg), lactose (75 mg) and magnesium stearate (15 mg). The mixture is passed through a 60 mesh sieve and packed into a No. 1 gelatin capsule.

A typical injectable preparation is produced by aseptically placing 250 mg of compounds of structure I into a vial, aseptically freeze-drying and sealing. For use, the contents of the vial are mixed with 2 mL of physiological saline, to produce an injectable preparation.

aP2 inhibitor activity of the compounds of the invention may be determined by use of an in vitro assay system which measures the potentiation of inhibition of aP2 by displacement of a fluorescent substrate from aP2 by the inhibitor. Inhibition constants (Ki values) for the aP2 inhibitors of the invention may be determined by the method described below:

Production of purified recombinant human aP2 protein. Recombinant human aP2 protein is produced by standard recombinant DNA technology. In the typical case, aP2 is produced by heterologous expression in *E. coli* strain BL21 (D53) transformed with pETila vector containing the full length human aP2 cDNA (Baxa, C. A., Sha, R. S., Buelt, M. K., Smith, A. J., Matarese, V., Chinander, L. L., Boundy, K. L., and Bernlohr, D. A. (1989). Human adipocyte lipid-binding protein: purification of the protein and cloning of its complementary DNA. Biochemistry 28: 8683–8690 and Xu, Z., Buelt, M. K., Banaszak, L. J., and Bernlohr, D. A. (1991). Expression, purification and crystallization of the adipocyte lipid binding protein. J. Biol. Chem. 266:14367–14370). Purification of aP2 from *E. coli* is conducted as described by Xu, yielding essentially homogeneous aP2 protein with molecular weight ~14600 daltons and free of endogenous fatty acids. The purified aP2 is capable of binding up to one mole of free fatty acid per mole protein. The binding and structural properties of recombinant aP2 protein were previously shown to be identical to aP2 protein isolated from adipose tissue.

In vitro assay of aP2 inhibitors. Inhibitors of aP2 are evaluated in a homogeneous fluorescent-based competition assay using recombinant aP2 protein and 1,8-anilino-naphthalene-sulfonic acid (1,8-ANS) as assay substrate. This competition assay was adapted from generalized procedures described previously (Kane, C. D. and Bernlohr, D. A. (1996). A simple assay for intracellular lipid-binding proteins using displacement of 1-anilino-8-sulfonic acid. (1996) Anal. Biochem. 233:197–204 and Kurian E., Kirk, W. R. and Prendergast, F. G. (1996) Affinity of fatty acid for r-rat intestinal fatty acid binding protein. Biochemistry, 35, 3865–3874). The method relies on the increase in fluorescence quantum yield of 1,8-ANS upon binding to the fatty acid binding site of aP2. The assay is run using appropriate concentrations of inhibitor, 1,8-ANS, and aP2 protein, in order to calculate the inhibitor binding constant (Ki) for compounds being evaluated. The Ki calculation was based on the procedure previously described for calculation of dissociation constants described by Kurian. Lower Ki values indicate higher affinities of compounds binding to aP2.

In the assay as conducted for the inhibitors described herein, a series of aliquots of aP2 (5 $\mu$M) in solution in 10 mM potassium phosphate buffer (pH 7.0) are mixed with an equimolar concentration of test compound, followed by the addition of a series of increasing concentrations of 1,8-ANS (from 0 to 5 $\mu$M). The assay typically is conducted in 96-well plate format with reagents added using robotic instrumentation (Packard Multiprobe 104). The fluorescence value for each test is determined using a Cytofluor-4000 multi-well fluorescence plate reader (Perceptive Biosystems) using excitation wavelength 360 nm and emission wavelength 460 nm, or using other suitable spectrofluorometer. In preparation for the assay, test compounds are initially prepared at 10 mM in dimethylsulfoxide. All subsequent dilutions and assay additions are made in 10 mM potassium phosphate buffer, pH 7.0.

X-ray crystallography of the inhibitor-aP2 complex can be performed by one skilled in the art using contemporary biophysical methodologies and commercial instrumentation. Such crystallographic data can be used to conclusively determine if a compound used in the present invention has embodied the structural requirement necessary for inhibition of aP2. An example of such an X-ray crystallographic determination is presented below:

Crystals of aP2 complexed with the inhibitors were typically grown by the hanging drop method. aP2, at 8.3 mg/ml, was pre-equilibrated with 1–5 mM of the inhibitor in 0.1 M Tris-HCl pH 8.0, 1% w/v DMSO for four hours. 2 µl drops containing equilibrated protein and reservoir solution at a 1:1 ratio were suspended on plastic cover slips and equilibrated against a 1 ml reservoir containing 2.6–3.0 M ammonium sulfate in 0.1 M Tris-HCl pH 8.0. Crystals typically appeared in 2–3 days and reached maximum size within 2 weeks. Data was typically collected on a single flash-frozen crystal (Oxford Cryosystems) using a Rigaku rotating anode and an R-axis II image plate detector of a Bruker multiwire area detector. Diffraction from aP2 crystals was excellent. Diffraction was consistently observed to better than 2.0 Å resolution often to beyond 1.5 Å resolution. Data was processed either with DENZO/SCALEPACK (R-axis II data), or Xengen (Bruker data). XPLOR was used for structure refinement and model building was done using the molecular modeling package CHAIN. After a single round of refinement, examination of the $F_o$-$F_c$ map typically allowed facile building of the inhibitor into aP2 binding cavity. Iterative fitting and refinement were continued until improvement was no longer seen in the electron density map or R-free.

The following Examples illustrate embodiments of the present invention, and are not intended to limit the scope of the claims. Abbreviations employed herein are defined below. Compounds of the Examples are identified by the example and step in which they are prepared (for example, "1A" denotes the title compounds of step A of Example 1), or by the example only where the compound is the title compound of the example (for example "4" denotes the title comound of Example 4).

9-BBN=9-borabicyclo[3.3.1]nonane
    Calc=calculated
    DiBA1=diisobutylaluminum hydride
    DMAP=Dimethylaminopyridine
    DMF=dimethylformamide
    DMSO=dimethylsulfoxide
    Et=ethyl
    Fnd=found
    h=hours
    LC/MS=liquid chromatography/mass spectrometry
    LDA=lithium diisopropylamide
    Me=methyl
    Ms=mesyl=methanesulfonyl
    OAc=acetate
    Ph=phenyl TFA=trifluoroacetic acid
THF=tetrahydrofuran
TMS=trimethylsilyl

EXAMPLE 1

5-(4-Bromophenyl)-1-[(2,4-dichlorophenyl)methyl]-1,6-dihydro-6-oxo-3-pyridine acetic acid

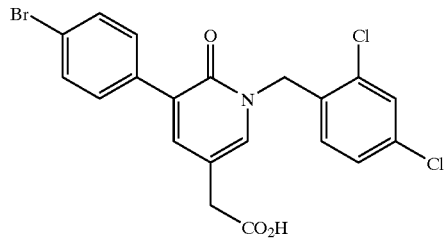

A. 1,6-Dihydro-5-iodo-6-oxo-3-pyridinecarboxylic acid ethyl ester

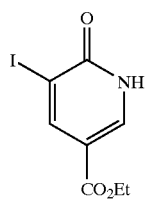

To a solution of ethyl 5-carboxy-2-pyridone (12.54 g, 75.0 mmol) in MeOH (150 mL) at room temperature under nitrogen, was added a N-iodosuccinimide (16.88 g, 75.0 mmol). The reaction mixture was heated to reflux for 18 h, cooled and poured into water (900 mL). The resulting solids were collected, dissolved in warm MeOH/EtOAc (1:19, 1200 ml) and washed once with 5% sodium thiosulfate solution in brine. The organic phase was dried (MgSO$_4$) and evaporated. The resulting solid was slurried in EtOAc (150 mL) and then hexanes (600 mL) were added. Filtration provided the title compound as a white solid, 18.83 g (86% yield). LC/MS gave the correct molecular ion [(M+H)$^+$= 294] for the desired compound.

B. 1-[(2,4-Dichlorophenyl)methyl]-1,6-dihydro-5-iodo-6-oxo-3-pyridinecarboxylic acid ethyl ester

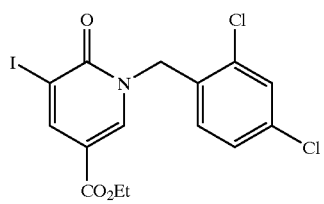

To a solution of 1A (10.0 g, 34.1 mmol) in DMF (100 mL) at room temperature under argon was added sodium hydride (1.48 g, 60% mineral oil dispersion, 37.0 mmol) portionwise over 5 min. After 15 min more, the resulting light yellow solution was treated with ethyl 2,4-dichlorophenylmethyl iodide (11.72 g, 40.9 mmol). The reaction mixture was heated to 60° C. for 15 min, then cooled to room temperature, quenched with 5% KHSO$_4$ solution and extracted twice with ether. The ether extracts were combined, washed twice with water, once with brine, dried (MgSO$_4$) and evaporated. Purification by flash chromatography on silica gel (12.5×30 cm column, 4:1 CH$_2$Cl$_2$/hexanes) gave the title compound as a white solid, 15.10 g, (98% yield). LC/MS gave the correct molecular ion [(M+H)$^+$=452] for the desired compound.

C. 5-(4-Bromophenyl)-1-[(2,4-dichlorophenyl)methyl]-1,6-dihydro-6-oxo-3-pyridinecarboxylic acid ethyl ester

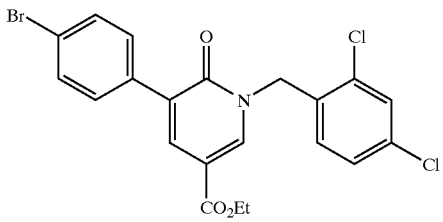

To a stirred solution of 1B (3.15 g, 7.0 mmol) in DMF (30 mL) at room temperature under argon was added 4-bromophenylboronic acid (1.55 g, 7.7 mmol), tri(o-tolyl)phosphene (145 mg, 0.5 mmol), triethylamine (2.95 mL, 21.2 mmol) and palladium (II) acetate (50 mg, 0.22 mmol). The reaction mixture was purged with an argon stream, then warmed to 55° C. for 36 h and then to 71° C. for 18 h. The reaction was cooled, quenched with saturated NaHCO$_3$ solution and extracted three times with ether. The organic extracts were combined, washed three times with water, once each with 10% citric acid solution and brine, dried (MgSO$_4$) and evaporated. The residue was purified by flash chromatography on silica gel (5×13 cm column, 1:2 hexanes/CH$_2$Cl$_2$) to give the title compound as a white solid, 1.74 g, (52% yield), mp 152–154 ° C. LC/MS gave the correct molecular ion [(M+H)$^+$=480] for the desired compound.

D. 5-(4-Bromophenyl)-1-[(2,4-dichlorophenyl)methyl]-1,6-dihydro-6-oxo-3-pyridinecarboxylic acid

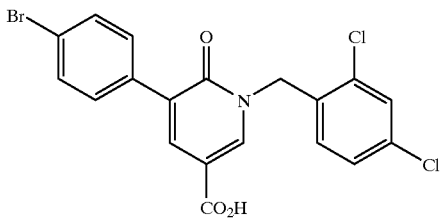

A solution of 1C (1.74 g, 3.62 mmol) in THF (10 mL) and MeOH (5 mL) was treated with sodium hydroxide solution (1.2 M, 5 mL, 6 mmol). The reaction mixture was heated to reflux for 3 h, cooled and evaporated to remove organic solvents. The aqueous residue was brought to pH 2 with 5 % KHSO$_4$ solution. The resulting precipitate was collected, washed with water and dried in vacuo to give the title compound as a white solid, 1.63 g, (99% yield), mp 137–139° C. LC/MS gave the correct molecular ion [(M+H)$^+$=452] for the desired compound.

E. 3-(4-Bromophenyl)-1-[(2,4-dichlorophenyl)methyl]-5-(hydroxymethyl)-2(1H)-pyridinone

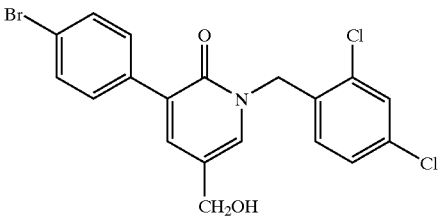

To a solution of 1D (2.707 g, 6.16 mmol) and trimethylborate (2.2 mL, 19 mmol) in THF (2 mL) at room temperature under argon was added borane dimethylsulfide complex (10 M, 0.60 mL, 6 mmol) at a rate to keep the temperature below 25° C. After 24 h, the reaction was quenched with MeOH and stirred for 1 h. The reaction mixture was evaporated and partitioned between EtOAc and saturated NaHCO$_3$ solution. The organic extract was dried (Na$_2$SO$_4$), evaporated and purified by flash chromatography on silica gel (5×25 cm column, 7:93 Et$_2$O/CH$_2$Cl$_2$ ) to give the title compound as a white solid, 1.42 g, (52% yield). LC/MS gave the correct molecular ion [(M+H)$^+$=438] for the desired compound.

F. 5-(Bromomethyl)-3-(4-bromophenyl)-1-[(2,4-dichlorophenyl)methyl]-2(1H)-pyridinone

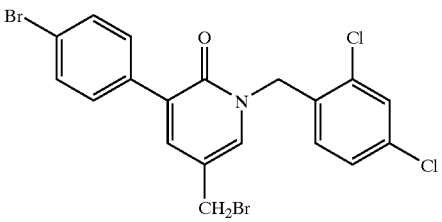

To a solution of 1E (666 mg, 1.51 mmol) in CH$_2$Cl$_2$ (6 mL) at room temperature under N$_2$, was added PBr$_3$ solution (1 M in CH$_2$Cl$_2$, 0.93 mL, 0.93 mmol). After 18 h, the reaction was quenched with NaHCO$_3$ solution and extracted with CH$_2$Cl$_2$ The organic extract was dried (MgSO$_4$) and evaporated to give the title compound as a waxy white solid, 754 mg, (99% yield). The compound is unstable and was used immediately in the following reaction.

G. 5-(4-Bromophenyl)-1-[(2,4-dichlorophenyl)methyl]-1,6-dihydro-6-oxo-3-pyridineacetonitrile

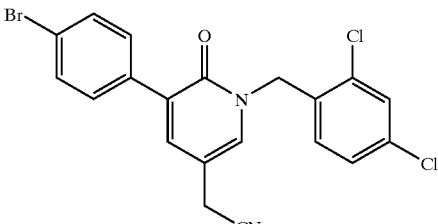

To a stirred solution of 1F (500 mg, 1.0 mmol) in DMF (3 mL) at room temperature under N$_2$ was added potassium cyanide (130 mg, 2.0 mmol). The reaction was heated at 50° C. After 5 min, the reaction was cooled and quenched with water. The resulting solids were collected, dissolved in CH$_2$Cl$_2$, dried (MgSO$_4$) and evaporated. Purification by flash chromatography (5×15 cm column, 1:79 ether/CH$_2$Cl$_2$) gave the title compound as a white foam, 210 mg (48% yield). LC/MS gave the correct molecular ion [(M+H)+= 447] for the desired compound.

H. 5-(4-Bromophenyl)-1-[(2,4-dichlorophenyl)methyl]-1,6-dihydro-6-oxo-3-pyridine acetic acid

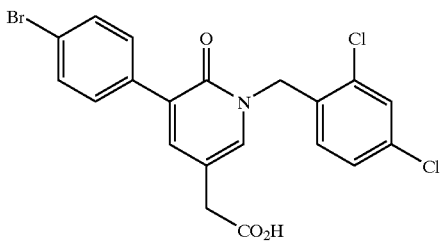

A stirred solution of 1G (175 mg, 0.4 mmol) in 1:1 TFA/concentrated hydrochloric acid (4 mL) was heated at reflux. After 14 h, the reaction mixture was cooled to room temperature and evaporated to dryness. Purification by flash chromatography on silica gel (2.5×20 cm column, EtOAc) provided the title compound as a tan solid, 168 mg (89% yield). LC/MS gave the correct molecular ion [(M+H)+= 466] for the desired compound.

We claim:

1. A compound of formula I:

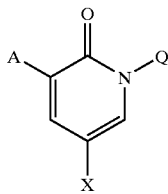

I or enantiomers, diastereomers, pharmaceutically acceptable salts and pro esters thereof wherein A is —$R^1$;
Q is —$(CR^3R^4)_n$—$R^2$ where a is 1;
X is $(CR^{3a}R^{4a})_n$—Z where a is 0 or 1;
$R^1$ is aryl, substituted aryl, heteroaryl, substituted heteroaryl, alkyl or cycloalkyl;
$R^2$ is aryl, substituted aryl, cycloalkylalkyl, heteroaryl or substituted heteroaryl;
$R^3$ and $R^4$ are the same or different and are selected from hydrogen, alkyl an substituted alkyl;
$R^{3a}$ and $R^{4a}$ are the same or different and are selected from hydrogen, hydra ,alkyl and substituted alkyl;
$R^9$ is H, alkyl, cycloalkyl, aryl, aralkyl, or heteroaryl;
Z is $CO_2R^9$, $CONH_2$, $PO_3H_2$, CONHOH, or tetrazole of the formula:

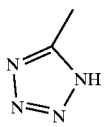

or its tautomer; and
n is an integer selected from 0 to 1 where each incidence of n is chosen independently.

2. The compound as defined in claim 1 wherein
$R^1$ is phenyl, or substituted phenyl
Q is $(CR^3R^4)_n$—$R^2$ where n is 1 and $R^3$ and $R^4$ are each hydrogen $R^2$ is phenyl, napthyl, substituted phenyl or substituted naptyl;
X is $(CR^{3a}R^4)_n$—Z where n is 0 or 1 and $R^{3a}$ and $R^{4a}$ are hydrogen; and
Z is $CO_2H$, or tetrazole.

3. The compound as defined in claim 2 wherein
$R^1$ is phenyl independently substituted with one or more halogen, alkoxy, or aryloxy;
$R^2$ is phenyl or napthyl independently substituted with one or more halogen, alkyl, substituted alkyl, alkoxy; arylalkoxy, aryloxy or cyano;
X is $(CR^{3a}R^{4a})_n$—Z where n is 1 and $R^{3a}$ and $R^{4a}$ are hydrogen; and
Z is $CO_2H$.

4. A compound of claim 1 selected from
5-(4-Bromophenyl)-1-[(2,4-dichlorophenyl)methyl]-1,6-dihydro-6-oxo-3-pyridine acetic acid;
5-(4-Bromophenyl)-1-[(2,4-dichlorophenyl)methyl]-1,6-dihydro-6-oxo-3-pyridinecarboxylic acid ethyl ester;
5-(4-Bromophenyl)-1-[(2,4-dichlorophenyl)methyl]-1,6-dihydro-6-oxo-3-pyridinecarboxylic acid; and
3-(4-Bromophenyl)-1-[(2,4-dichlorophenyl)methyl]-5-(hydroxymethyl)-2(1H)-pyridinone.

5. A compound of formula II:

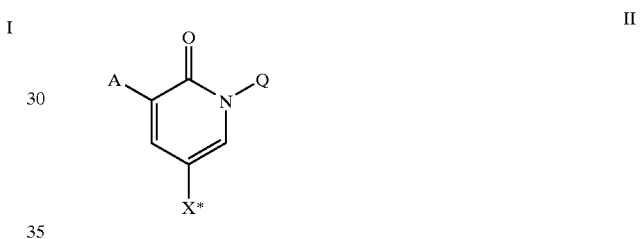

II or enantiomers, diastereomers, and salts thereof wherein
A is selected from
—$R^1$
Q is selected from
—$(CR^3R^4)_n$—$R^2$, where n is 1;
$R^1$ is aryl, substituted aryl, heteroaryl, substituted heteroaryl, alkyl or cycloalkyl;
$R^2$ is aryl, substituted aryl, cycloalkylalkyl, heteroaryl or substituted heteroaryl;
$R^3$ and $R^4$ are the same or different and are selected from hydrogen, alkyl an substituted alkyl;
$R^{3a}$ and $R^{4a}$ are the same or different and are selected from hydrogen, hydroxy, alkyl and substituted alkyl;
$R^9$ is H, alkyl, cycloalkyl, aryl, aralkyl, or heteroaryl;
X* is —$(CR^{3a}R^{4a})_n$—W;
W is cyano, C(O)Cl, or C(O)H; and
n is an integer selected from 0 to 1 where each incidence of n is chosen independently.

6. The compound as defined in claim 5 wherein
$R^1$ is phenyl, or substituted phenyl
Q is $(CR^3R^4)_n$—$R^2$ where n is 1 and $R^3$ and $R^4$ are each hydrogen
$R^2$ is phenyl, napthyl, substituted phenyl or substituted napthyl.

7. The compound as defined in claim 6 wherein
$R^1$ is phenyl independently substituted with one or more halogen, alkoxy, or aryloxy; and
$R^2$ is phenyl or napthyl independently substituted with one or more halogen, alkyl, substituted alkyl, alkoxy; arylalkoxy, aryloxy or cyano.

8. A pharmaceutical composition comprising at least one compound of claim 1 and a pharmaceutically acceptable carrier therefor.

9. A pharmaceutical combination comprising at least one compound of claim 1, at least one other antidiabetic agent, and a pharmaceutically acceptable carrier therefor.

10. The combination of claim 9 wherein the other antidiabetic agent is a biguanide, a sulfonyl urea, a glucosidase inhibitor, a thiazolidinedione, an insulin sensitizer, a glucagon-like peptide-1 (GLP-1), or insulin.

11. The combination of claim 10 wherein the antidiabetic agent is metformin, glyburide, glimepiride, glipyride, glipizide, chlorpropamide, gliclazide, acarbose, miglitol, troglitazone, rosiglitizone, and/or insulin.

12. The combination of claim 10 wherein the pound is present in a weight ratio to the antidiabetic agent within the range from about 0.01:1 to about 100:1.

13. A method for treating insulin resistance, hyperglycemia, hyperinsulinemia, or elevated blood levels of free fatty acids or glycerol, obesity, hypertriglyceridemia, inflammation, atherosclerosis, diabetic retinopathy, diabetic neuropathy or diabetic nephropathy which comprises administering to a mammalian specie in need thereof an effective amount of the pharmaceutical composition of claim 8.

14. A method for treating insulin resistance, hyperglycemia, hyperinsulinemia, or elevated blood levels of free fatty acids or glycerol, obesity, hypertriglyceridemia, inflammation, atherosclerosis, diabetic retinopathy, diabetic neuropathy or diabetic nephropathy which comprises administering to a mammalian species in need thereof an effective amount of the pharmaceutical composition of claim 9.

* * * * *